(12) United States Patent
Kang et al.

(10) Patent No.: US 11,191,440 B2
(45) Date of Patent: Dec. 7, 2021

(54) ELECTRONIC DEVICE COMPRISING PLURALITY OF LIGHT SOURCES

(71) Applicant: Samsung Electronics Co., Ltd., Gyeonggi-do (KR)

(72) Inventors: Seunggoo Kang, Gyeonggi-do (KR); Dongil Son, Gyeonggi-do (KR); Junghoon Park, Gyeonggi-do (KR)

(73) Assignee: Samsung Electronics Co., Ltd

( * ) Notice: Subject to any disclaimer, the term of this patent is extended or adjusted under 35 U.S.C. 154(b) by 329 days.

(21) Appl. No.: 16/359,189

(22) Filed: Mar. 20, 2019

(65) Prior Publication Data

US 2019/0290148 A1 Sep. 26, 2019

(30) Foreign Application Priority Data

Mar. 20, 2018 (KR) .......................... 10-2018-0031872

(51) Int. Cl.
  *G01B 11/24* (2006.01)
  *A61B 5/024* (2006.01)
  (Continued)

(52) U.S. Cl.
  CPC ........ *A61B 5/02433* (2013.01); *A61B 5/0075* (2013.01); *A61B 5/6898* (2013.01);
  (Continued)

(58) Field of Classification Search
  CPC ... G01B 11/2536; G01B 11/245; G01B 11/25; G01C 11/02; G06T 7/0057
  (Continued)

(56) References Cited

U.S. PATENT DOCUMENTS 7,819,311 B2  10/2010  Rowe et al.
9,970,816 B2  5/2018  Roentgen et al.
(Continued)

FOREIGN PATENT DOCUMENTS

CN  103281459  9/2013
CN  104825131  8/2015
(Continued)

OTHER PUBLICATIONS

Kim Beom-Su, ICT Research Institute, "Dummy's ICT Trend Story", Jan. 23, 2017, http://blog.naver.com/PostPrint.nhn?blogId=baemsu&logNo=220917895699 pp. 1-3.
(Continued)

*Primary Examiner* — Md M Rahman
(74) *Attorney, Agent, or Firm* — The Farrell Law Firm, P.C.

(57) ABSTRACT

An electronic device includes a light emitter emitting visible light, an infrared emitter emitting infrared light, at least one detector detecting an electromagnetic wave, and at least one processor configured to obtain a user input to obtain spectral data of a target object, in response to obtaining the user input, emit the visible light by using the light emitter and emit the infrared light by using the infrared emitter, obtain a first reflected signal of the visible light reflected by the target object and a second reflected signal of the infrared light reflected by the target object, using the at least one detector, and generate the spectral data of the target object based on the first reflected signal and the second reflected signal.

20 Claims, 7 Drawing Sheets

(51) Int. Cl.
  *H04N 5/225* (2006.01)
  *G01J 3/28* (2006.01)
  *A61B 5/00* (2006.01)
  *G01J 3/42* (2006.01)

(52) U.S. Cl.
  CPC ............ *A61B 5/742* (2013.01); *G01J 3/2823* (2013.01); *G01J 3/42* (2013.01); *H04N 5/2256* (2013.01)

(58) Field of Classification Search
  USPC ........................................................ 356/610
  See application file for complete search history.

(56) References Cited

U.S. PATENT DOCUMENTS

| | | | |
|---|---|---|---|
| 10,031,587 | B2 | 7/2018 | Heo |
| 10,429,298 | B2 | 10/2019 | Vauclin et al. |
| 2004/0240712 | A1 | 12/2004 | Rowe et al. |
| 2005/0185847 | A1 | 8/2005 | Rowe |
| 2010/0297291 | A1 | 11/2010 | Shinoda et al. |
| 2011/0261355 | A1 | 10/2011 | Hannel et al. |
| 2015/0173631 | A1* | 6/2015 | Richards ............ A61B 5/02427 600/479 |
| 2015/0223749 | A1 | 8/2015 | Park et al. |
| 2016/0109959 | A1 | 4/2016 | Heo |
| 2017/0248467 | A1 | 8/2017 | Roentgen et al. |
| 2017/0303790 | A1 | 10/2017 | Bala et al. |
| 2018/0020964 | A1* | 1/2018 | Newberry ................ A61B 5/01 600/301 |
| 2018/0284020 | A1 | 10/2018 | Vauclin et al. |

FOREIGN PATENT DOCUMENTS

| | | |
|---|---|---|
| CN | 106068446 | 11/2016 |
| JP | 2014-211418 | 11/2014 |
| KR | 1020130133949 | 12/2013 |
| WO | WO 2009/038206 | 3/2009 |
| WO | WO 2017/055580 | 4/2017 |

OTHER PUBLICATIONS

European Search Report dated Dec. 11, 2020 issued in counterpart application No. 19771521.2-1132, 7 pages.
Chinese Office Action dated Jan. 22, 2021 issued in counterpart application No. 201980013325.4, 26 pages.
International Search Report dated Jul. 9, 2019 issued in counterpart application No. PCT/KR2019/003249, 13 pages.

* cited by examiner

ELECTRONIC DEVICE COMPRISING PLURALITY OF LIGHT SOURCES

CROSS-REFERENCE TO RELATED APPLICATION(S)

This application is based on and claims priority under 35 U.S.C. § 119 to Korean Patent Application No. 10-2018-0031872, filed on Mar. 20, 2018, in the Korean Intellectual Property Office, the disclosure of which is incorporated herein by reference in its entirety.

BACKGROUND

1. Field

The present disclosure relates generally to a technology for a spectrometer.

2. Description of Related Art

A spectrometer is an optical sensor composed of an emitter and a light receiving part. The spectrometer is used in various fields, such as a field for analyzing the composition of a substance, as well as various medical fields. For example, the spectrometer may be used to measure a skin condition and to calculate the sugar content of fruit. In recent years, the spectrometer has been miniaturized to be capable of being mounted in a small device such as a smart phone.

A light source with a wavelength range of about 300 nm to about 1050 nm may be required to implement the spectrometer. As such, a lamp-type light emitting diode (LED) or a plurality of chip LEDs may be used as a light source. However, the size of the lamp-type LED may be large and a lot of mounting space may be required where the plurality of chip LEDs are mounted. Accordingly, the lamp-type LED or the chip LEDs may not be suitable to be mounted on a small device, such as a smart phone.

Accordingly, it may be advantageous to provide an electronic device capable of performing a spectrometer function, using one or more light sources already mounted without having to mount a separate spectrometer.

SUMMARY

The present disclosure has been made to address the above-mentioned problems and disadvantages, and to provide at least the advantages described below.

In accordance with an aspect of the present disclosure, an electronic device includes a first emitter emitting a first electromagnetic wave corresponding to a first wavelength range, a second emitter emitting a second electromagnetic wave corresponding to a second wavelength range, at least one detector configured to detect an electromagnetic wave, and at least one processor. The at least one processor may be configured to obtain a user input to obtain spectral data of a target object outside the electronic device, emit the first electromagnetic wave and the second electromagnetic wave by using the first emitter and the second emitter, in response to obtaining the user input, obtain a first reflected signal of the first electromagnetic wave and a second reflected signal of the second electromagnetic wave, which are reflected by the target object, using the at least one detector, and obtain the spectral data of the target object based on the first reflected signal and the second reflected signal.

In accordance with an aspect of the present disclosure, an electronic device includes a light emitter emitting visible light, an infrared emitter emitting infrared light, at least one detector detecting an electromagnetic wave, and at least one processor. The at least one processor may be configured to obtain a user input to obtain spectral data of a target object, in response to obtaining the user input, emit the visible light by using the light emitter and emit the infrared light by using the infrared emitter, obtain a first reflected signal of the visible light reflected by the target object and a second reflected signal of the infrared light reflected by the target object, using the at least one detector, and generate the spectral data of the target object based on the first reflected signal and the second reflected signal.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
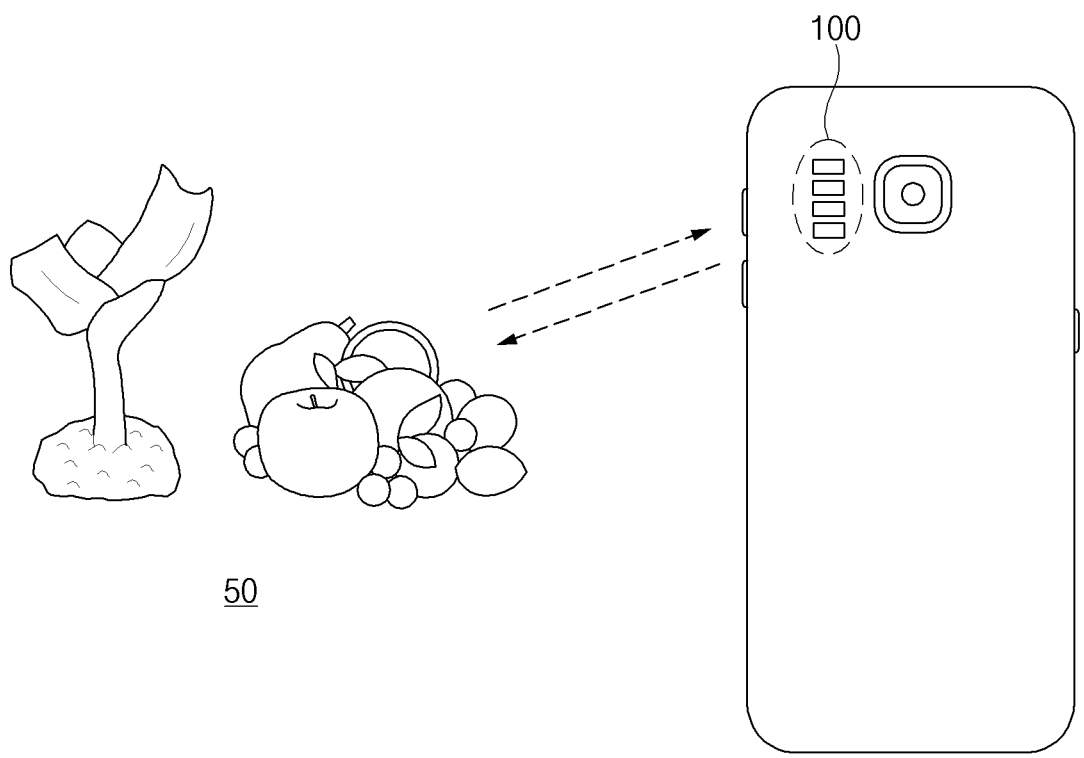
FIG. 1 is a view illustrating an operating environment of an electronic device, according to an embodiment.

Various embodiments of the present disclosure are described with reference to the accompanying drawings. However, various embodiments of the present disclosure are not limited to particular embodiments, and it should be understood that modifications, equivalents, and/or alternatives of the embodiments described herein can be variously made. With regard to description of drawings, similar components may be marked by similar reference numerals.

FIG. 1 is a view illustrating an operating environment of an electronic device, according to an embodiment.

Referring to FIG. 1, an electronic device 10 may operate as a spectrometer. The electronic device 10 may obtain spectral data of a target object 50 using a plurality of light sources and a light receiving part 100 mounted on the electronic device 10.

The electronic device 10 may emit electromagnetic waves including infrared and visible light, using a plurality of light sources. For example, the electromagnetic waves may emit the electromagnetic waves to the target object 50.

The target object 50 is a target object, of which the spectral data is to be obtained by the user. For example, the user may cause the light source of the electronic device 10 to face the target object 50. As such, the electronic device 10 may emit electromagnetic waves to the target object 50. The electronic device 10 may obtain a signal reflected by the target object 50, using the light receiving part 100. The electronic device 10 may generate spectral data for the target object 50 based on the obtained reflected signal.

A plurality of light sources and the light receiving part 100 may be included in various components mounted on the electronic device 10. For example, a plurality of light sources and the light receiving part 100 may be included in a general camera which includes a flash, a three-dimensional (3D) camera, or a biometric sensor (e.g., a heart sensor). The electronic device 10 may operate as a spectrometer using components already mounted thereon.

Figure 2:
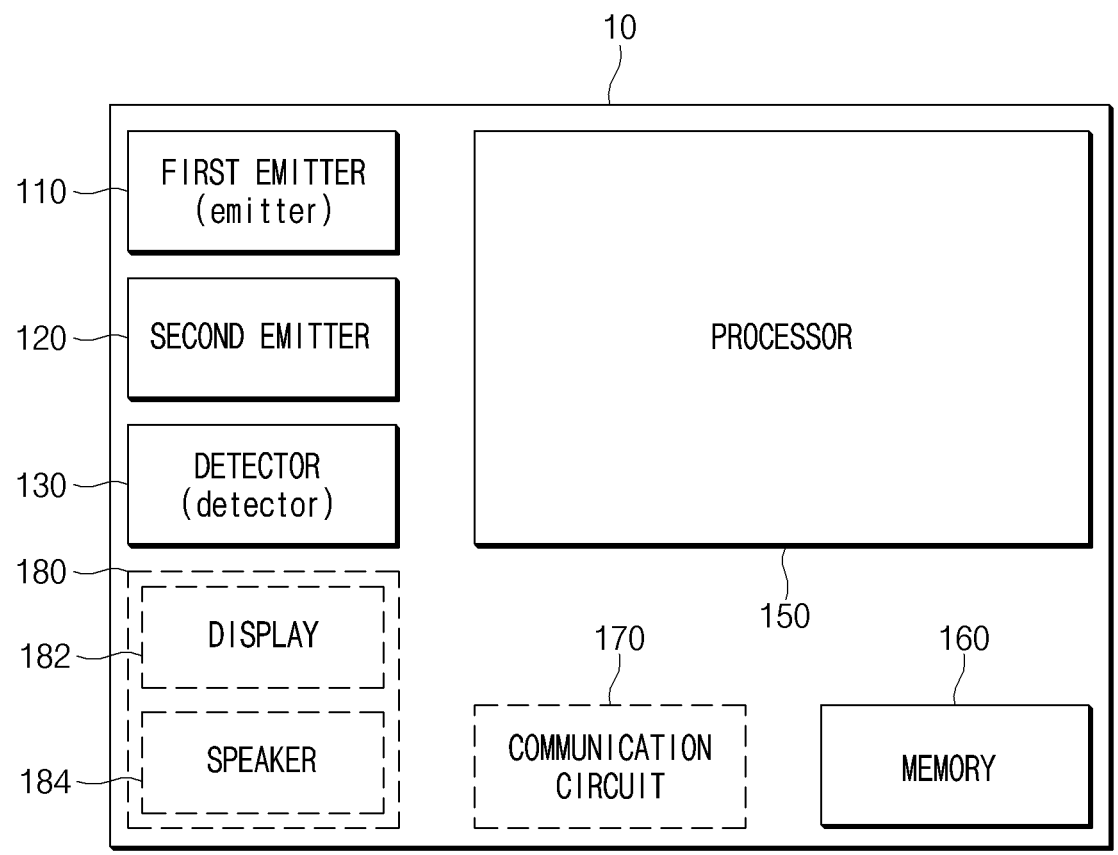
FIG. 2 is a block diagram of the electronic device, according to an embodiment.

FIG. 2 is a block diagram of the electronic device, according to an embodiment.

Referring to FIG. 2, the electronic device 10 includes a processor 150, a first emitter 110, a second emitter 120, and a detector 130. Each of the first emitter 110 and the second emitter 120 may be referred to as a light source; the detector 130 may be referred to as a light receiving part.

The processor 150 of the electronic device 10 may control overall operations of the electronic device 10. The processor 150 may be electrically connected to the first emitter 110, the second emitter 120, and the detector 130. The processor 150 may perform the operation of the electronic device 10, using the first emitter 110, the second emitter 120, and the detector 130. The processor 150 may be referred to as an application processor (AP).

The first emitter 110 and the second emitter 120 may emit electromagnetic waves of wavelength bands different from each other. For example, the first emitter 110 may be configured to emit a first electromagnetic wave corresponding to a first wavelength range, and the second emitter 120 may be configured to emit a second electromagnetic wave corresponding to a second wavelength range. For example, the first wavelength range may include the range from about 420 nm to about 680 nm (i.e., the first wavelength range may be 400 nm to 680 nm, thereby including the range of about 420 nm to about 680 nm), and thus the first electromagnetic wave may include visible light. The second wavelength range may include at least a part of the range from about 700 nm to about 1 mm (i.e., the second wavelength range may be 700 nm to 980 nm, thereby including a part of the range from about 700 nm to about 1 mm), and thus the second electromagnetic wave may include infrared light.

The detector 130 may be configured to detect electromagnetic waves and may be implemented with a plurality of detectors. When the detector 130 is implemented with a plurality of detectors, each of the detectors may be configured to detect electromagnetic waves of wavelengths different from each other. For example, the detector 130 may detect visible light and infrared light. The electronic device 10 may generate spectral data for the target object 50 based on the reflected signal obtained through the detector 130.

The electronic device 10 may provide a user with the result of analyzing the generated spectral data. For example, a memory 160 of the electronic device 10 may store spectral information. The spectral information may be referenced by a predetermined spectrum analyzing method that depends on the type of the target object 50. For example, Table 1 illustrates the type of the target object 50 that reacts to each wavelength of light. The spectral information may include the target object 50, the wavelength band at which the target object 50 reacts, and the analyzing method. The electronic device 10 may provide the user with the analysis information corresponding to the spectral data generated based on the spectral information.

TABLE 1

| Target object 50 | Heart rate/ stress | Sugar content of fruit | Skin moisture | Subcu- taneous fat | Protein | Carbo- hydrate |
|---|---|---|---|---|---|---|
| Wave- length (nm) | About 880 | About 850- 1000 | About 900- 1000 | About 850- 1000 | About 300 | About 660 |

The electronic device 10 may further include a communication circuit 170 for communicating with an external server. The electronic device 10 may transmit the generated spectral data to the external server and may provide the analysis information received from the external server to the user. The external server may be a server that stores information for analyzing spectral data and provides analysis results.

The electronic device 10 may further include an output device 180, such as a display 182 and a speaker 184. For example, the electronic device 10 may visually display the analysis result of the spectral data through the display 182 or may play the analysis result as a voice message through the speaker 184.

The electronic device 10 may obtain information about what type of target object 50 is to be analyzed by the user. For example, the electronic device 10 may recognize the target object 50 through an image analyzing method and utilize a well-known image analyzing method. The electronic device 10 may store an image analyzing module in the memory 160 or may communicate with an external server that provides an image analyzing service. Alternatively, the electronic device 10 may receive information about the target object 50 from the user. For example, the user may enter information about the target object 50 input as an utterance or text.

The electronic device 10 may generate analysis information using information about the target object 50. Alternatively, the electronic device 10 may provide information about the target object 50 to an external server together with spectral data.

Figure 3:
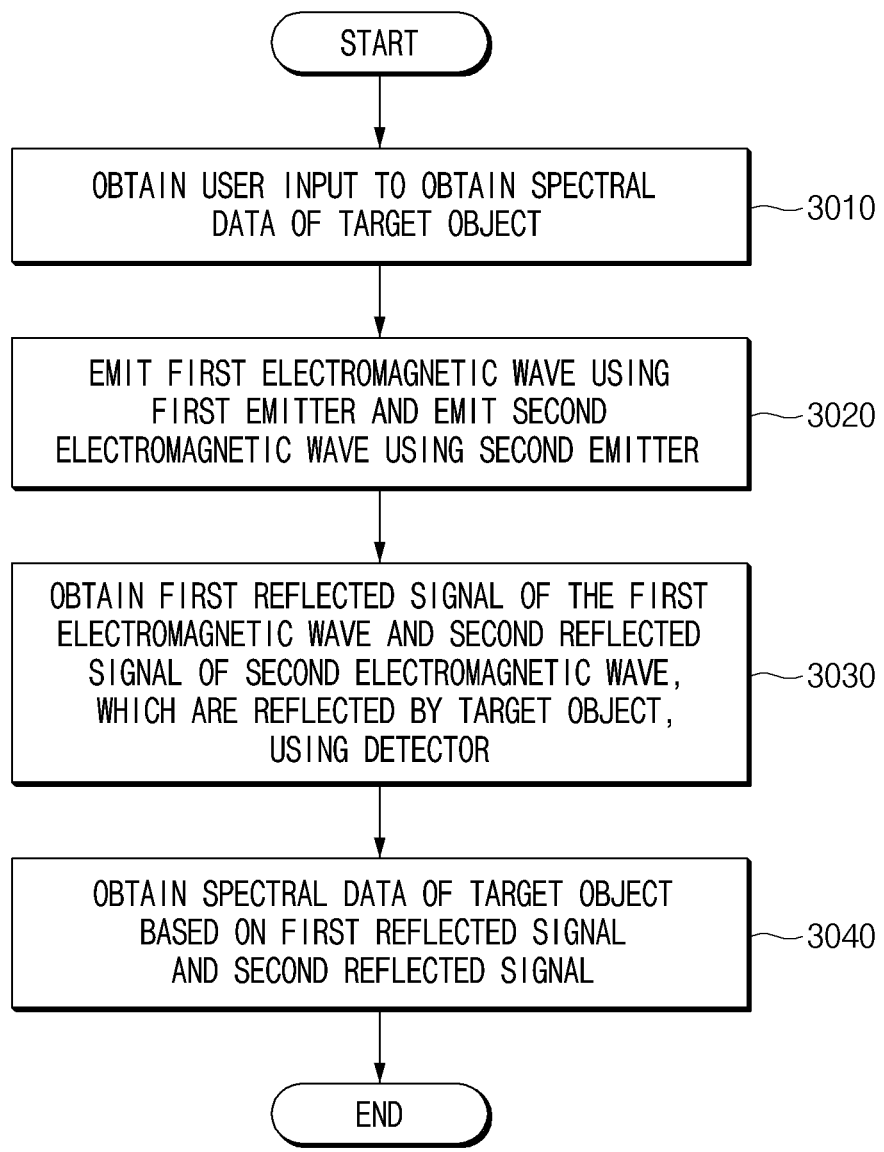
FIG. 3 is a flowchart of a method of performing a function of a spectrometer, according to an embodiment.

FIG. 3 is a flowchart of a method of performing a function of a spectrometer, according to an embodiment.

The method of performing the function of a spectrometer shown in FIG. 3 may be performed by, for example, the electronic device 10 illustrated in FIG. 2.

Referring to FIG. 3, Steps 3010-3040 may be implemented with instructions capable of being performed (or executed) by the processor 150 of the electronic device 10. The instructions may be stored in, for example, a computer-readable recording medium or the memory 160 of the electronic device 10 illustrated in FIG. 2. Hereinafter, descriptions of the elements of FIG. 2 will not be repeated when steps 3010-3040 of FIG. 3 directly or indirectly reference an element of FIG. 2.

In step 3010, the electronic device 10 obtains a user input to obtain spectral data of the target object 50. For example, the electronic device 10 may output an interface, which allows the spectrometer function to start, through the output device 180, and the user may click on a start button of the interface, or may vocally enter a keyword such as "start". A click input or a vocal input may be referred to as a user input.

In step 3020, the electronic device 10 emits a first electromagnetic wave using the first emitter 110 and emits a second electromagnetic wave using the second emitter 120, in response to obtaining the user input. For example, the first electromagnetic wave and the second electromagnetic wave may be emitted towards the target object 50.

The first emitter 110 may be referred to as a light emitter configured to emit visible light. The second emitter 120 may be referred to as an infrared emitter configured to emit infrared light. However, the first and second electromagnetic waves may have arbitrary wavelength bands between about 300 nm to about 1050 nm. Thus, the first emitter is not limited to a light emitter and the second emitter is not limited to an infrared emitter.

In step 3030, the electronic device 10 obtains a first reflected signal of the first electromagnetic wave and a second reflected signal of the second electromagnetic wave, which are reflected by (i.e., off of) the target object 50, using the detector 130. For example, the first reflected signal may be referred to as a reflected signal of visible light, and the second reflected signal may be referred to as a reflected signal of infrared light.

In step 3040, the electronic device 10 obtains the spectral data of the target object 50 based on the first reflected signal and the second reflected signal through the detector 130. For example, the spectral data may be referred to as spectral data from the wavelength area of the visible light to the wavelength area of the infrared light.

The electronic device 10 may provide a result of analyzing the spectral data through the output device 180, as described with reference to FIG. 2.

Figure 4:
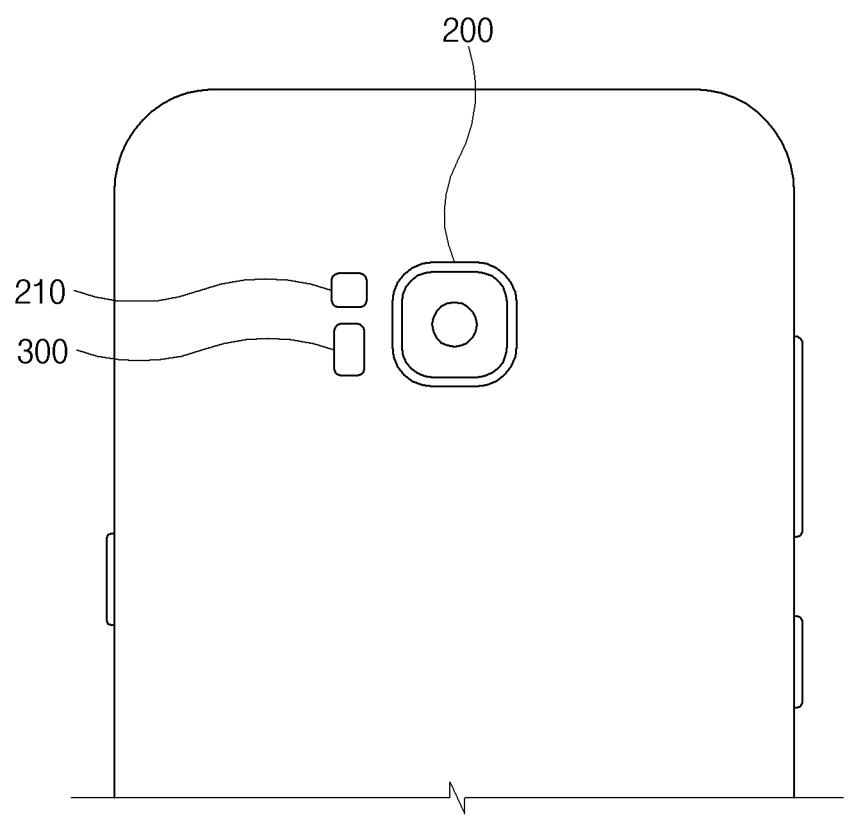
FIG. 4 is a view illustrating a structure of an electronic device, according to an embodiment.
Figure 5:
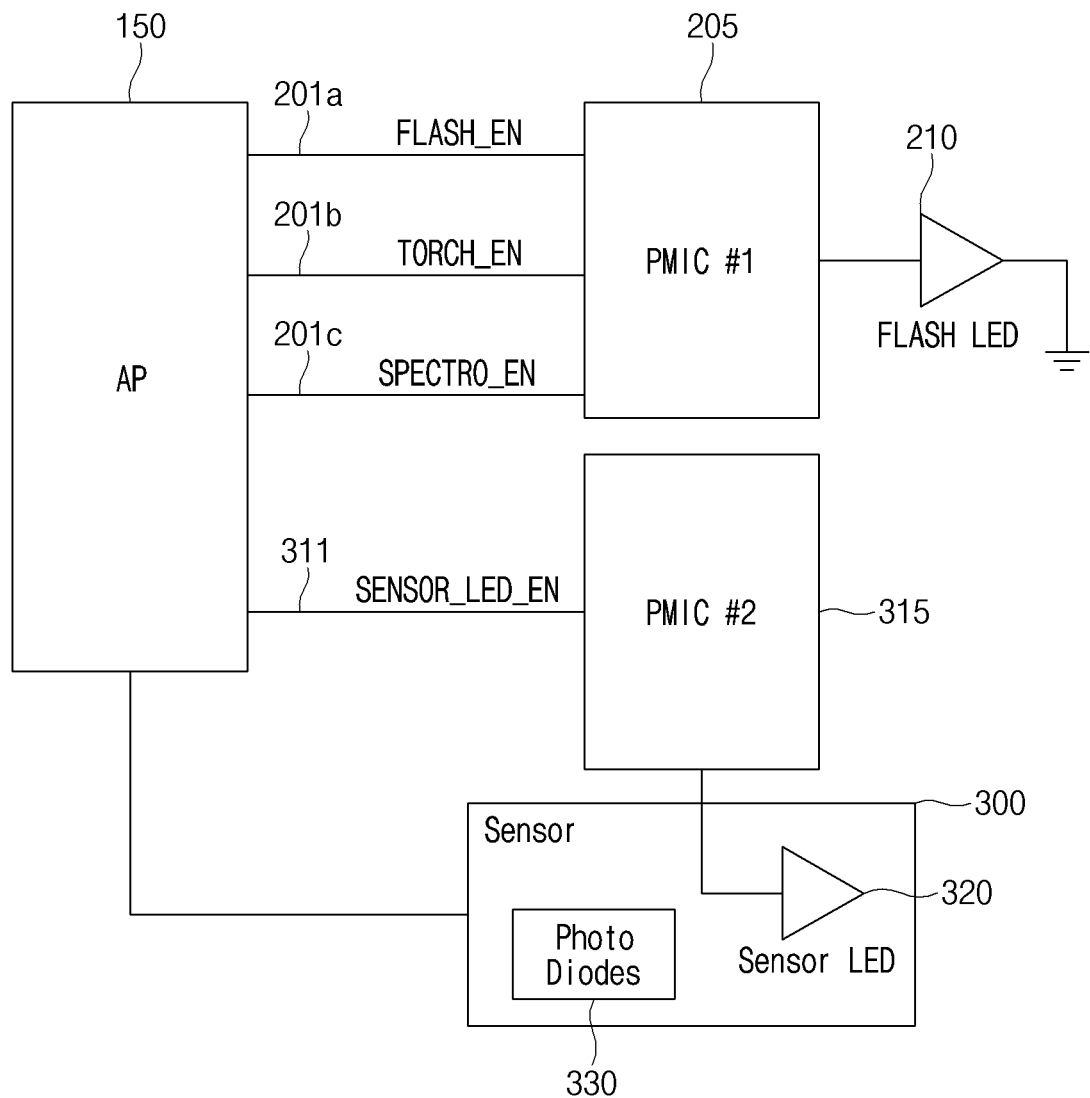
FIG. 5 is a diagram illustrating a circuit disposed inside an electronic device, according to an embodiment.

FIG. 4 is a view illustrating a structure of an electronic device, according to an embodiment. FIG. 5 is a diagram illustrating a circuit disposed inside an electronic device, according to an embodiment.

Referring to FIGS. 4 and 5, an electronic device 10 may include a camera 200, a light emitter 210 (e.g., a flash LED) for the camera 200, and a biometric sensor 300 (e.g., a heart rate sensor). The biometric sensor 300 may include an infrared emitter 320 (e.g., infrared LED) and a detector 330 (e.g., a photo diode). The electronic device 10 may perform the spectrometer function using the light emitter 210 and the biometric sensor 300.

The light emitter 210 may be referred to as a light emitter (e.g., the first emitter 110 of FIG. 2) configured to emit visible light. The infrared emitter 320 of the biometric sensor 300 may be referred to as an infrared emitter configured to emit infrared light (e.g., the second emitter 120 of FIG. 2). The detector 330 may be configured to detect infrared light and visible light.

The electronic device 20 may include a 3D camera (e.g., a face recognition camera) configured to emit infrared light. In this case, the electronic device 10 may perform the spectrometer function using the 3D camera and the flash of the 3D camera. In this case, the 3D camera may further include a detector configured to detect visible light and infrared light.

The electronic device 20 may include at least one light source configured to emit visible light and/or infrared light and at least one detector configured to detect visible light and/or infrared light. The electronic device 10 may selectively emit at least one light source and may perform the function of a spectrometer by obtaining the reflected signal through a detector.

Hereinafter, an embodiment is described in which the electronic device 20 performs the function of a spectrometer by using the camera 200 and the biometric sensor 300. However, alternative embodiments may be realized. For example, the electronic device 20 may perform the same function using a light source and a detector, which are mounted on the electronic device 20.

The electronic device 20 may include the processor 150, the light emitter 210, a first power management circuit 205 supplying current to the light emitter 210, the infrared emitter 320, a second power management circuit 315 supplying current to the infrared emitter 320, and a detector 330.

The electronic device 20 may obtain a user input to obtain spectral data of the target object 50. The electronic device 20 may emit visible light by using the light emitter 210 of the camera 200 in response to obtaining the user input, and may emit infrared light by using the infrared emitter 320 of the biometric sensor 300. The visible light and the infrared light may be emitted towards the target object.

The electronic device 20 may obtain the spectral data of the target object based on the first reflected signal of the visible light reflected from the target object and the second reflected signal of the infrared light reflected from the target object.

For the purpose of matching the amount of the light emitted by the light emitter 210 and the amount of the light emitted by the infrared emitter 320, the electronic device 20 may control the intensity of the current applied to the light emitter 210 and/or the infrared emitter 320.

Generally, the amount of light emitted from the light emitter 210 (flash LED) of the camera 200 may be set to be relatively strong compared to that of the infrared emitter 320 of the biometric sensor 300. That is, the infrared emitter 320 of the biometric sensor 300 may be configured to emit a relatively low amount of light, considering that infrared light penetrates the human body. As such, when the electronic device 10 applies the same intensity of current to the camera 200 and the light emitter 210, saturation may occur in the detector 330 when a spectrometer function is performed. Accordingly, for the purpose of obtaining spectral data, the electronic device 20 may control the light emitter 210 to emit less light when performing a spectrometer function than when performing a function of the camera 200.

For the purpose of performing a flash function using the light emitter 210, the electronic device 20 may apply a first current to the light emitter 210 of the camera 200 using the first power management circuit 205. For the purpose of obtaining a reflected signal for the visible light, the electronic device 20 may apply a second current having a magnitude less than the first current for the flash function, to the light emitter 210 by using the first power management circuit 205.

Figure 6:
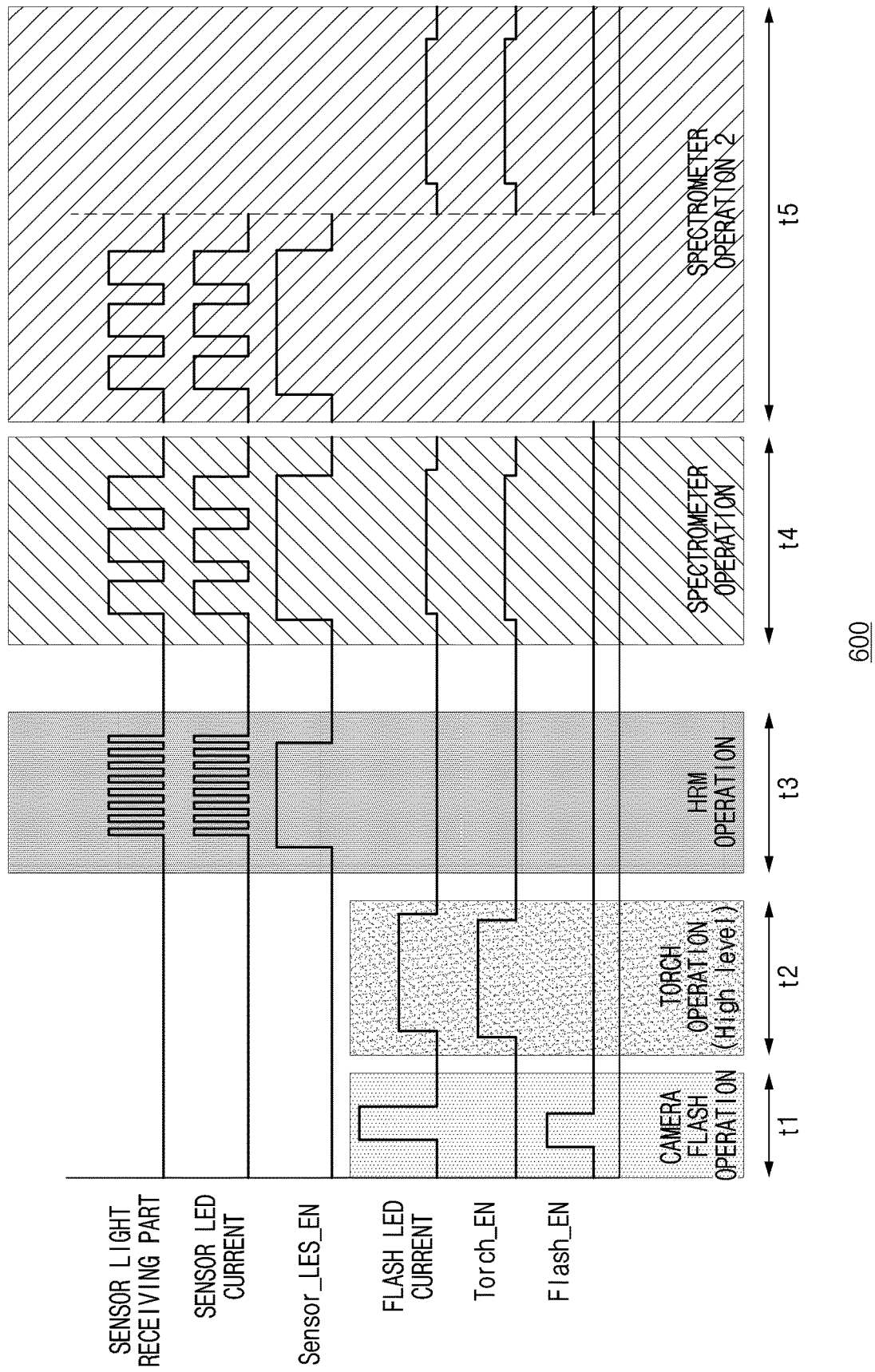
FIG. 6 is a diagram for describing an operation of an electronic device, according to an embodiment.

FIG. 6 is a diagram for describing an operation of an electronic device, according to an embodiment. Hereinafter, the operation of an electronic device will be described with reference to FIGS. 5 and 6.

The light emitter 210 of the camera may have a flash function and a torch function. For example, the electronic device 20 may apply a first enable signal through a first electrical path 201*a* such that the light emitter 210 performs the flash function. The electronic device 20 may apply a second enable signal through a second electrical path 201*b* such that the light emitter 210 performs the torch function. The first enable signal may have a pulse of a period shorter than the second enable signal. Moreover, the electronic device 20 may apply a fourth enable signal through a fourth electrical path 311 to operate the infrared emitter 320 of the biometric sensor 300. The first power management circuit 205 may be configured to supply current to the light emitter 210 in response to the receipt of an enable signal. The second power management circuit 315 may be configured to supply current to the infrared emitter 320 in response to the receipt of the enable signal. The light emitter 210 and the infrared emitter 320 may operate based on respective enable signals.

For example, referring to section t1, the electronic device 20 may apply a first enable signal, which has a short period when its level is set to high, to the first power management circuit 205 such that the light emitter 210 performs the flash function. As such, the first power management circuit 205 may supply high intensity current to the light emitter 210 for a short period and the current may flow to the anode terminal of the light emitter 210.

Referring to section t2, the electronic device 20 may apply a second enable signal, which has a long period when its level is set to high, to the first power management circuit 205 such that the light emitter 210 performs the torch function. As such, the first power management circuit 205 may supply high intensity current to the light emitter 210 for a long period and the current may flow to the anode terminal of the light emitter 210.

Referring to section t3, the electronic device 20 may apply a fourth enable signal to the second power management circuit 315 to operate the biometric sensor 300. As such, the second power management circuit 315 may supply current to the infrared emitter 320 and the current may flow to the anode terminal of the biometric sensor 300. A driver for the infrared emitter 320 in the biometric sensor 300 may control a cathode terminal.

Referring to section t4, for the purpose of performing the spectrometer function, the electronic device 20 may apply a third enable signal, which has a level that is set lower than the respective levels of the first enable signal and the second enable signal, to the first power management circuit 205 for a long period similar to the period of the second enable signal of the first power management circuit 205. For example, for the purpose of performing the spectrometer function, the electronic device 20 may apply the third enable signal to the first power management circuit 205 through a third electrical path 201c. As such, the first power management circuit 205 may supply the current corresponding to the enable signal to the light emitter 210. At approximately the same time, the electronic device 20 may apply the fourth enable signal to the second power management circuit 315. As such, the second power management circuit 315 may supply the current corresponding to the fourth enable signal to the infrared emitter 320. Referring to section t5, after the electronic device 20 applies the third enable signal to the first power management circuit 205, the electronic device 20 may apply the fourth enable signal to the second power management circuit 315. The electronic device 20 may obtain first spectral data using the reflected signal of the visible light of the light emitter 210, and may obtain second spectral data using the reflected signal of the infrared light of the infrared emitter 320. The electronic device 20 may extract first data of the wavelength band of the visible light area from the first spectral data, may extract second data of the wavelength band of the infrared light area from the second spectral data, and may merge the first data and the second data.

The electronic device 20 may selectively emit the light emitter 210 and the infrared emitter 320 depending on the target wavelength area. For example, when the target object reacts at about 500 nm, the electronic device 20 may only operate the light emitter 210 and may provide the analysis result, using the spectral data obtained therefrom.

Figure 7:
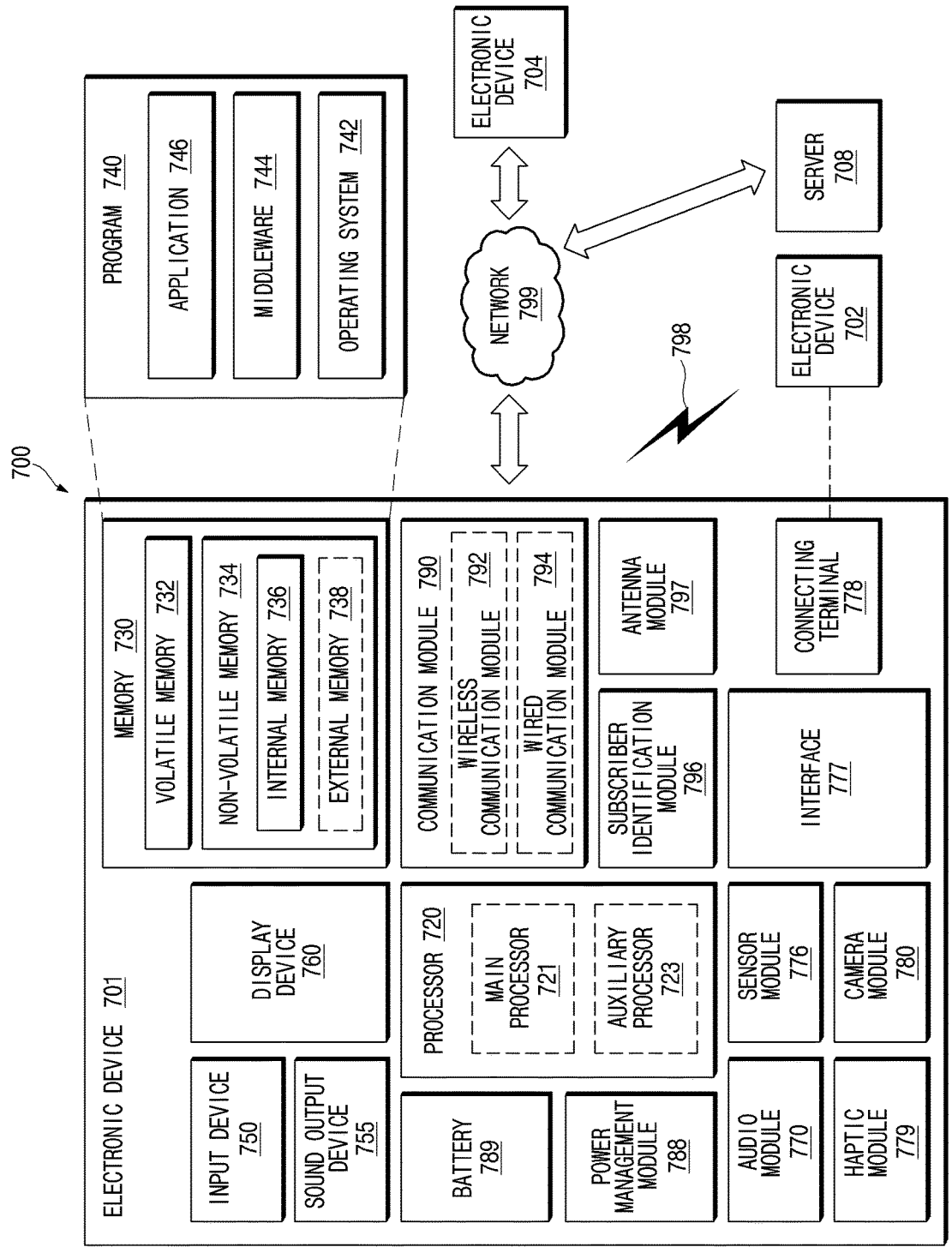
FIG. 7 illustrates an electronic device in a network environment, according to various embodiments.

FIG. 7 is a block diagram illustrating an electronic device 701 in a network environment 700 according to various embodiments. Referring to FIG. 7, the electronic device 701 in the network environment 700 may communicate with an electronic device 702 via a first network 798 (e.g., a short-range wireless communication network), or an electronic device 704 or a server 708 via a second network 799 (e.g., a long-range wireless communication network). According to an embodiment, the electronic device 701 may communicate with the electronic device 704 via the server 708. According to an embodiment, the electronic device 701 may include a processor 720, memory 730, an input device 750, a sound output device 755, a display device 760, an audio module 770, a sensor module 776, an interface 777, a haptic module 779, a camera module 780, a power management module 788, a battery 789, a communication module 790, a subscriber identification module (SIM) 796, or an antenna module 797. In some embodiments, at least one (e.g., the display device 760 or the camera module 780) of the components may be omitted from the electronic device 701, or one or more other components may be added in the electronic device 701. In some embodiments, some of the components may be implemented as single integrated circuitry. For example, the sensor module 776 (e.g., a fingerprint sensor, an iris sensor, or an illuminance sensor) may be implemented as embedded in the display device 760 (e.g., a display).

The processor 720 may execute, for example, software (e.g., a program 740) to control at least one other component (e.g., a hardware or software component) of the electronic device 701 coupled with the processor 720, and may perform various data processing or computation. According to one embodiment, as at least part of the data processing or computation, the processor 720 may load a command or data received from another component (e.g., the sensor module 776 or the communication module 790) in volatile memory 732, process the command or the data stored in the volatile memory 732, and store resulting data in non-volatile memory 734. According to an embodiment, the processor 720 may include a main processor 721 (e.g., a central processing unit (CPU) or an application processor (AP)), and an auxiliary processor 723 (e.g., a graphics processing unit (GPU), an image signal processor (ISP), a sensor hub processor, or a communication processor (CP)) that is operable independently from, or in conjunction with, the main processor 721. Additionally or alternatively, the auxiliary processor 723 may be adapted to consume less power than the main processor 721, or to be specific to a specified function. The auxiliary processor 723 may be implemented as separate from, or as part of the main processor 721.

The auxiliary processor 723 may control at least some of functions or states related to at least one component (e.g., the display device 760, the sensor module 776, or the communication module 790) among the components of the electronic device 701, instead of the main processor 721 while the main processor 721 is in an inactive (e.g., sleep) state, or together with the main processor 721 while the main processor 721 is in an active state (e.g., executing an application). According to an embodiment, the auxiliary processor 723 (e.g., an image signal processor or a communication processor) may be implemented as part of another component (e.g., the camera module 780 or the communication module 790) functionally related to the auxiliary processor 723.

The memory 730 may store various data used by at least one component (e.g., the processor 720 or the sensor module 776) of the electronic device 701. The various data may include, for example, software (e.g., the program 740) and input data or output data for a command related thereto. The memory 730 may include the volatile memory 732 or the non-volatile memory 734.

The program 740 may be stored in the memory 730 as software, and may include, for example, an operating system (OS) 742, middleware 744, or an application 746.

The input device 750 may receive a command or data to be used by another component (e.g., the processor 720) of the electronic device 701, from the outside (e.g., a user) of the electronic device 701. The input device 750 may include, for example, a microphone, a mouse, or a keyboard.

The sound output device 755 may output sound signals to the outside of the electronic device 701. The sound output device 755 may include, for example, a speaker or a receiver. The speaker may be used for general purposes, such as playing multimedia or playing record, and the receiver may be used for an incoming call. According to an embodiment, the receiver may be implemented as separate from, or as part of the speaker.

The display device 760 may visually provide information to the outside (e.g., a user) of the electronic device 701. The display device 760 may include, for example, a display, a hologram device, or a projector and control circuitry to control a corresponding one of the display, hologram device, and projector. According to an embodiment, the display device 760 may include touch circuitry adapted to detect a touch, or sensor circuitry (e.g., a pressure sensor) adapted to measure the intensity of force incurred by the touch.

The audio module 770 may convert a sound into an electrical signal and vice versa. According to an embodiment, the audio module 770 may obtain the sound via the input device 750, or output the sound via the sound output device 755 or a headphone of an external electronic device (e.g., an electronic device 702) directly (e.g., wiredly) or wirelessly coupled with the electronic device 701.

The sensor module 776 may detect an operational state (e.g., power or temperature) of the electronic device 701 or an environmental state (e.g., a state of a user) external to the electronic device 701, and then generate an electrical signal or data value corresponding to the detected state. According to an embodiment, the sensor module 776 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 777 may support one or more specified protocols to be used for the electronic device 701 to be coupled with the external electronic device (e.g., the electronic device 702) directly (e.g., wiredly) or wirelessly. According to an embodiment, the interface 777 may include, for example, a high definition multimedia interface (HDMI), a universal serial bus (USB) interface, a secure digital (SD) card interface, or an audio interface.

A connecting terminal 778 may include a connector via which the electronic device 701 may be physically connected with the external electronic device (e.g., the electronic device 702). According to an embodiment, the connecting terminal 778 may include, for example, a HDMI connector, a USB connector, a SD card connector, or an audio connector (e.g., a headphone connector), The haptic module 779 may convert an electrical signal into a mechanical stimulus (e.g., a vibration or a movement) or electrical stimulus which may be recognized by a user via his tactile sensation or kinesthetic sensation. According to an embodiment, the haptic module 779 may include, for example, a motor, a piezoelectric element, or an electric stimulator.

The camera module 780 may capture a still image or moving images. According to an embodiment, the camera module 780 may include one or more lenses, image sensors, image signal processors, or flashes.

The power management module 788 may manage power supplied to the electronic device 701. According to one embodiment, the power management module 788 may be implemented as at least part of, for example, a power management integrated circuit (PMIC).

The battery 789 may supply power to at least one component of the electronic device 701. According to an embodiment, the battery 789 may include, for example, a primary cell which is not rechargeable, a secondary cell which is rechargeable, or a fuel cell.

The communication module 790 may support establishing a direct (e.g., wired) communication channel or a wireless communication channel between the electronic device 701 and the external electronic device (e.g., the electronic device 702, the electronic device 704, or the server 708) and performing communication via the established communication channel. The communication module 790 may include one or more communication processors that are operable independently from the processor 720 (e.g., the application processor (AP)) and supports a direct (e.g., wired) communication or a wireless communication. According to an embodiment, the communication module 790 may include a wireless communication module 792 (e.g., a cellular communication module, a short-range wireless communication module, or a global navigation satellite system (GNSS) communication module) or a wired communication module 794 (e.g., a local area network (LAN) communication module or a power line communication (PLC) module). A corresponding one of these communication modules may communicate with the external electronic device via the first network 798 (e.g., a short-range communication network, such as Bluetooth™, wireless-fidelity (Wi-Fi) direct, or infrared data association (IrDA)) or the second network 799 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 792 may identify and authenticate the electronic device 701 in a communication network, such as the first network 798 or the second network 799, using subscriber information (e.g., international mobile subscriber identity (IMSI)) stored in the subscriber identification module 796.

The antenna module 797 may transmit or receive a signal or power to or from the outside (e.g., the external electronic device) of the electronic device 701. According to an embodiment, the antenna module 797 may include one or more antennas, and, therefrom, at least one antenna appropriate for a communication scheme used in the communication network, such as the first network 798 or the second network 799, may be selected, for example, by the communication module 790 (e.g., the wireless communication module 792). The signal or the power may then be transmitted or received between the communication module 790 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 701 and the external electronic device 704 via the server 708 coupled with the second network 799. Each of the electronic devices 702 and 704 may be a device of a same type as, or a different type, from the electronic device 701. According to an embodiment, all or some of operations to be executed at the electronic device 701 may be executed at one or more of the external electronic devices 702, 704, or 708. For example, if the electronic device 701 should perform a function or a service automatically, or in response to a request from a user or another device, the electronic device 701, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 701. The electronic device 701 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 740) including one or more instructions that are stored in a storage medium (e.g., internal memory 736 or external memory 738) that is readable by a machine (e.g., the electronic device 701). For example, a processor (e.g., the processor 720) of the machine (e.g., the electronic device 701) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

As described herein, because a function of a spectrometer may be implemented using already mounted parts, a separate mounting space for a spectrometer may not be required, and the manufacturing cost of an electronic device may be reduced.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
a first emitter configured to emit a first electromagnetic wave corresponding to a first wavelength range;
a second emitter configured to emit a second electromagnetic wave corresponding to a second wavelength range;
a power management circuit configured to supply current to the first emitter;
at least one detector configured to detect an electromagnetic wave; and
at least one processor configured to:
obtain a user input to obtain spectral data of a target object outside the electronic device,
emit the first electromagnetic wave and the second electromagnetic wave by using the first emitter and the second emitter, in response to obtaining the user input,
obtain a first reflected signal of the first electromagnetic wave and a second reflected signal of the second electromagnetic wave, which are reflected by the target object, using the at least one detector,
obtain the spectral data of the target object based on the first reflected signal and the second reflected signal,
apply first current to the first emitter by using the power management circuit such that the first emitter performs a flash function or a torch function, and
apply second current having intensity less than the first current, to the first emitter by using the power management circuit to obtain the first reflected signal by using the at least one detector such that the first emitter performs a spectrometer function.

2. The electronic device of claim 1, wherein the first wavelength range includes a range of at least 420 nanometer (nm) to 680 nm, and
wherein the second wavelength range includes a part of a range of at least 700 nm to 1 millimeter (mm).

3. The electronic device of claim 2, further comprising:
a camera including the first emitter; and
a heart rate sensor including the second emitter and the at least one detector,
wherein the at least one processor is further configured to, in response to obtaining the user input, emit visible light by using the first emitter of the camera, and emit infrared light by using the second emitter of the heart rate sensor.

4. The electronic device of claim 3,
wherein the at least one processor is further configured to:
apply the first current to the first emitter by using the power management circuit to obtain an image by using the camera.

5. The electronic device of claim 1, wherein the at least one processor is further configured to selectively detect the first reflected signal or the second reflected signal based on the target object by using the at least one detector.

6. The electronic device of claim 1, further comprising an output device,
wherein the at least one processor is further configured to display analysis information about the spectral data through the output device.

7. An electronic device comprising:
a light emitter configured to emit visible light;
an infrared emitter configured to emit infrared light;
a power management circuit configured to supply current to the light emitter;
at least one detector configured to detect an electromagnetic wave; and
at least one processor configured to:
obtain a user input to obtain spectral data of a target object,
in response to obtaining the user input, emit the visible light by using the light emitter and emit the infrared light by using the infrared emitter,
obtain a first reflected signal of the visible light reflected by the target object and a second reflected signal of the infrared light reflected by the target object, using the at least one detector,
generate the spectral data of the target object based on the first reflected signal and the second reflected signal,
apply first current to the light emitter by using the power management circuit such that the light emitter performs a flash function or a torch function, and
apply second current having intensity less than the first current, to the light emitter by using the power management circuit to obtain the first reflected signal by using the at least one detector such that the light emitter performs a spectrometer function.

8. The electronic device of claim 7, wherein the at least one processor is further configured to:
after emitting the visible light by using the light emitter, obtain the first reflected signal by using the at least one detector, and obtain first spectral data of the target object based on the first reflected signal,
emit the infrared light by using the infrared emitter,
obtain the second reflected signal by using the at least one detector,
obtain second spectral data of the target object based on the second reflected signal, and
obtain the spectral data based on the first spectral data and the second spectral data.

9. The electronic device of claim 8, wherein the at least one processor is further configured to merge the first spectral data and the second spectral data.

10. The electronic device of claim 9, wherein the at least one processor is further configured to:
extract first data of a visible light wavelength band of the first spectral data,
extract second data of an infrared light wavelength band of the second spectral data, and
merge the first data and the second data.

11. The electronic device of claim 7, wherein the at least one processor is further configured to selectively detect the first reflected signal or the second reflected signal by using the at least one detector, based on the target object.

12. The electronic device of claim 7, further comprising:
a display; and
a memory including spectral information,
wherein the at least one processor is further configured to display analysis information about the spectral data generated based on the spectral data and the spectral information, through the display.

13. The electronic device of claim 12, wherein the at least one processor is further configured to:
obtain an input of information about the target object, and
display the analysis information generated based on the information about the target object, the spectral data, and the spectral information, through the display.

14. The electronic device of claim 7, further comprising:
a display; and
a communication circuit configured to communicate with an external server, wherein the at least one processor is further configured to:
   transmit the spectral data to the external server through the communication circuit, and
   display analysis information corresponding to the spectral data received from the external server, through the display.

15. The electronic device of claim 14, wherein the at least one processor is further configured to:
   obtain an input of information about the target object, and
   transmit the information about the target object and the spectral data to the external server through the communication circuit.

16. The electronic device of claim 7, further comprising:
   a camera including the light emitter; and
   a heart rate sensor including the infrared emitter and the at least one detector,
   wherein the at least one processor is further configured to in response to obtaining the user input, emit the visible light by using the light emitter of the camera, and emit the infrared light by using the infrared emitter of the heart rate sensor.

17. The electronic device of claim 16,
   wherein the at least one processor is further configured to:
      apply the first current to the light emitter of the camera by using the power management circuit to obtain an image by using the camera.

18. The electronic device of claim 17, further comprising a first electrical path and a second electrical path, which are positioned between the at least one processor and the power management circuit,
   wherein the at least one processor is further configured to:
      apply a first enable signal corresponding to the first current to the power management circuit through the first electrical path, and
      apply a second enable signal corresponding to the second current to the power management circuit through the second electrical path.

19. The electronic device of claim 7, further comprising a camera including the light emitter, the infrared emitter, and the at least one detector.

20. The electronic device of claim 7, wherein the at least one detector includes a first detector configured to detect the visible light and a second detector configured to detect the infrared light, and
   wherein the electronic device further comprises:
      a camera including the light emitter and the first detector; and
      a heart rate sensor including the infrared emitter and the second detector.

* * * * *